(12) United States Patent
Jong et al.

(10) Patent No.: US 6,710,197 B1
(45) Date of Patent: Mar. 23, 2004

(54) METHOD FOR THE PREPARATION OF COPPER (METH) ACRYLOYLOXYETHYL PHOSPHATE COORDINATION COMPLEX

(75) Inventors: Shean-Jeng Jong, Tao-Yuan (TW); Chong Ma, Tao-Yuan (TW)

(73) Assignee: Chung-Shan Institute of Science and Technology, Tao-Yuan (TW)

( * ) Notice: Subject to any disclaimer, the term of this patent is extended or adjusted under 35 U.S.C. 154(b) by 0 days.

(21) Appl. No.: 10/291,390

(22) Filed: Nov. 12, 2002

(51) Int. Cl.[7] .................................................. C07F 1/08

(52) U.S. Cl. ......................................... 556/24; 556/117

(58) Field of Search ................................... 556/24, 117

(56) References Cited

U.S. PATENT DOCUMENTS

| 4,296,214 A | * 10/1981 | Kamada et al. ............. 524/398 |
| 5,466,755 A | * 11/1995 | Sakagami et al. ........ 525/326.6 |

FOREIGN PATENT DOCUMENTS

| WO | WO97/28226 | * 8/1997 |
| WO | WO99/26951 | * 6/1999 |

* cited by examiner

*Primary Examiner*—Porfirio Nazario-Gonzalez
(74) *Attorney, Agent, or Firm*—Bacon & Thomas, PLLC

(57) ABSTRACT

A compound capable of efficiently cutting off light in the near infrared region, copper (meth)acryloyloxyethyl phosphate coordination complex, is synthesized including reacting (meth)acryloyloxyethyl phosphate and copper acetate monohydrate in water.

9 Claims, 4 Drawing Sheets

METHOD FOR THE PREPARATION OF COPPER (METH) ACRYLOYLOXYETHYL PHOSPHATE COORDINATION COMPLEX

FIELD OF THE INVENTION

The present invention is related to a method for the preparation of copper (meth)acryloyloxyethyl phosphate coordination complex, which is useful for cutting off light in the near infrared region, and in particular to a method for the preparation of copper (meth)acryloyloxyethyl phosphate coordination complex by using water as a solvent.

BACKGROUND OF THE INVENTION

PCT application WO 99/26951 (1999) discloses a copper (meth)acryloyloxyethyl phosphate coordination complex having the formula (I), which can be used to form an optical filter film for cutting off near-IR ray, or as a near-IR-absorbing agent in a coating composition:

$R_{3-n}PO(O^{31})_nCu(II)$        (I)

wherein R is $CH_2=C(CH_3)COOCH_2CH_2O$, and n is 1 or 2. This complex is synthesized by reacting a mixture of $H_3PO_4$ mono- and di-ester of 2-hydroxyethyl (meth)acrylate having the formula (II) with Cu acetate monohydrate having the following formula (III) in an organic solvent of methyl ethyl ketone as shown in the following reaction:

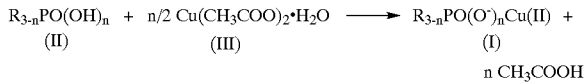

$R_{3-n}PO(OH)_n$ + $n/2$ $Cu(CH_3COO)_2 \cdot H_2O \longrightarrow R_{3-n}PO(O^-)_nCu(II)$ +
(II)        (III)                              (I)
                                                      n $CH_3COOH$ wherein R and n are defined as above. This synthesis method uses an organic solvent detrimental to the environment and the operator, however.

SUMMARY OF THE INVENTION

The present invention provides a synthesis method for the complex having the above formula (I) without using an organic solvent, which comprises reacting a $H_3PO_4$ ester of 2-hydroxyethyl (meth)acrylate having the above formula (II) with the Cu acetate monohydrate having the above formula (III) in water. The complex (I) can be obtained after evaporating water and the resulting acetic acid. The synthesis method of the present invention does not use an organic solvent, and thus does not have drawbacks caused by the organic solvent.

Preferably, a mixture of $H_3PO_4$ mono- and di-ester of 2-hydroxyethyl (meth)acrylate with n=1 and n=2 in the formula (II) is reacted with the Cu acetate monohydrate (III) to form a mixture of complex compounds with n=1 and n=2 in the formula (I). In one of the preferred embodiments of the present invention said mixture of $H_3PO_4$ mono- and di-ester of 2-hydroxyethyl (meth)acrylate having a molar ratio of the $H_3PO_4$ di-ester of 2-hydroxyethyl (meth)acrylate, n=1, to the $H_3PO_4$ mono-ester of 2-hydroxyethyl (meth)acrylate, n=2, is about 0.4.

A suitable amount of the Cu acetate monohydrate (III) used in said reaction is 1%–1000%, preferably 40–90%, based on mole of the $H_3PO_4$ ester (II). Preferably, an excess amount of the $H_3PO_4$ ester (II) is used in said reaction.

A suitable amount of water used in said reaction is 0.5–100, preferably 3–4, times of weight of said $H_3PO_4$ ester (II).

Said reaction of the present invention may be carried out at a temperature between 0–100° C. and preferably about 25–60° C.

DETAILED DESCRIPTION OF PREFERRED EMBODIMENTS

The present invention can be better understood by the following examples which are illustrative only, not for limiting the scope of the present invention.

EXAMPLE 1

Figure 1:
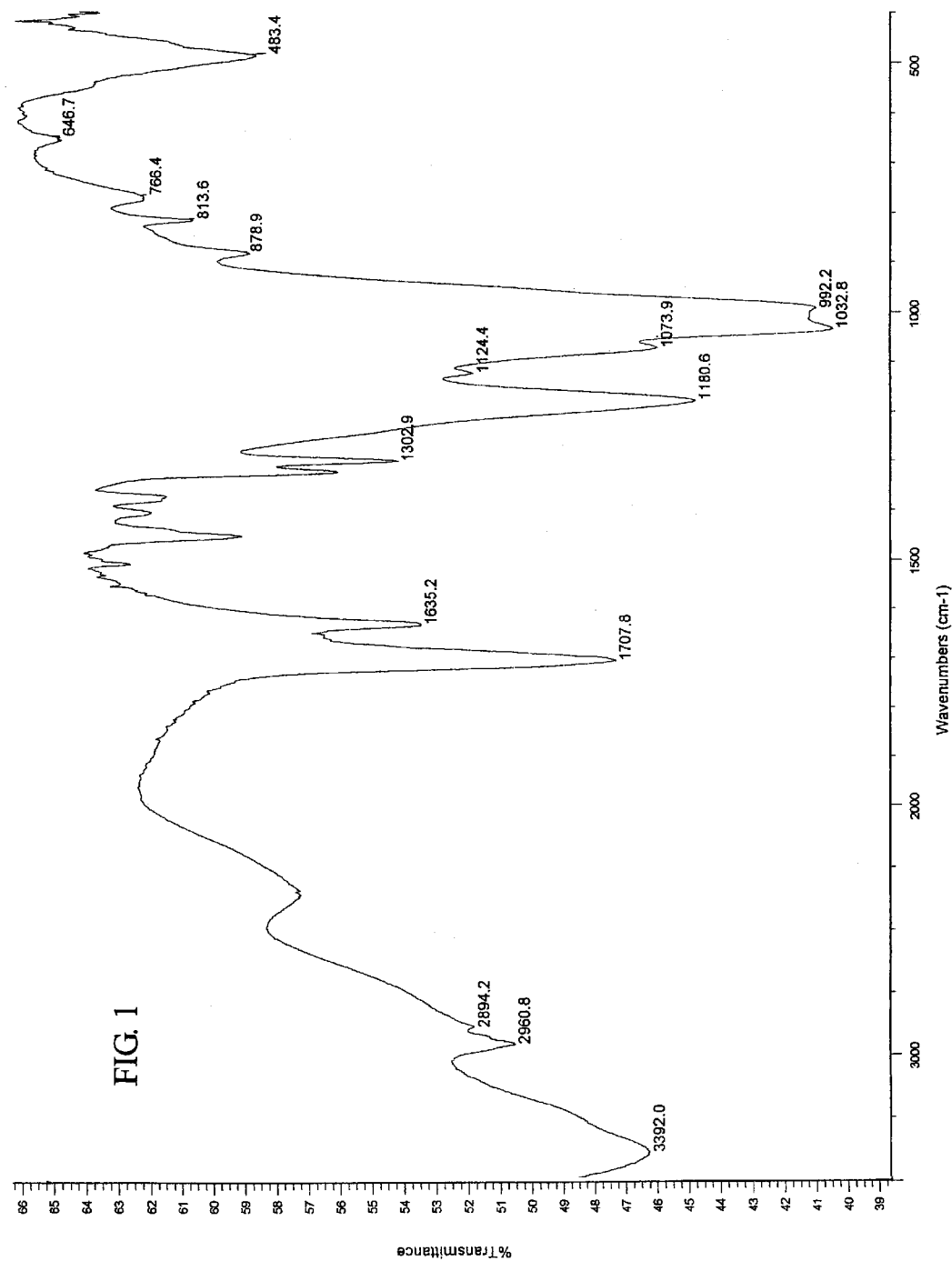
FIG. 1 is an infrared spectrum of a mixture of $H_3PO_4$ mono- and di-ester of 2-hydroxyethyl (meth)acrylate with n=1 and n=2 in the formula (II) used in the method of the present invention
Figure 2:
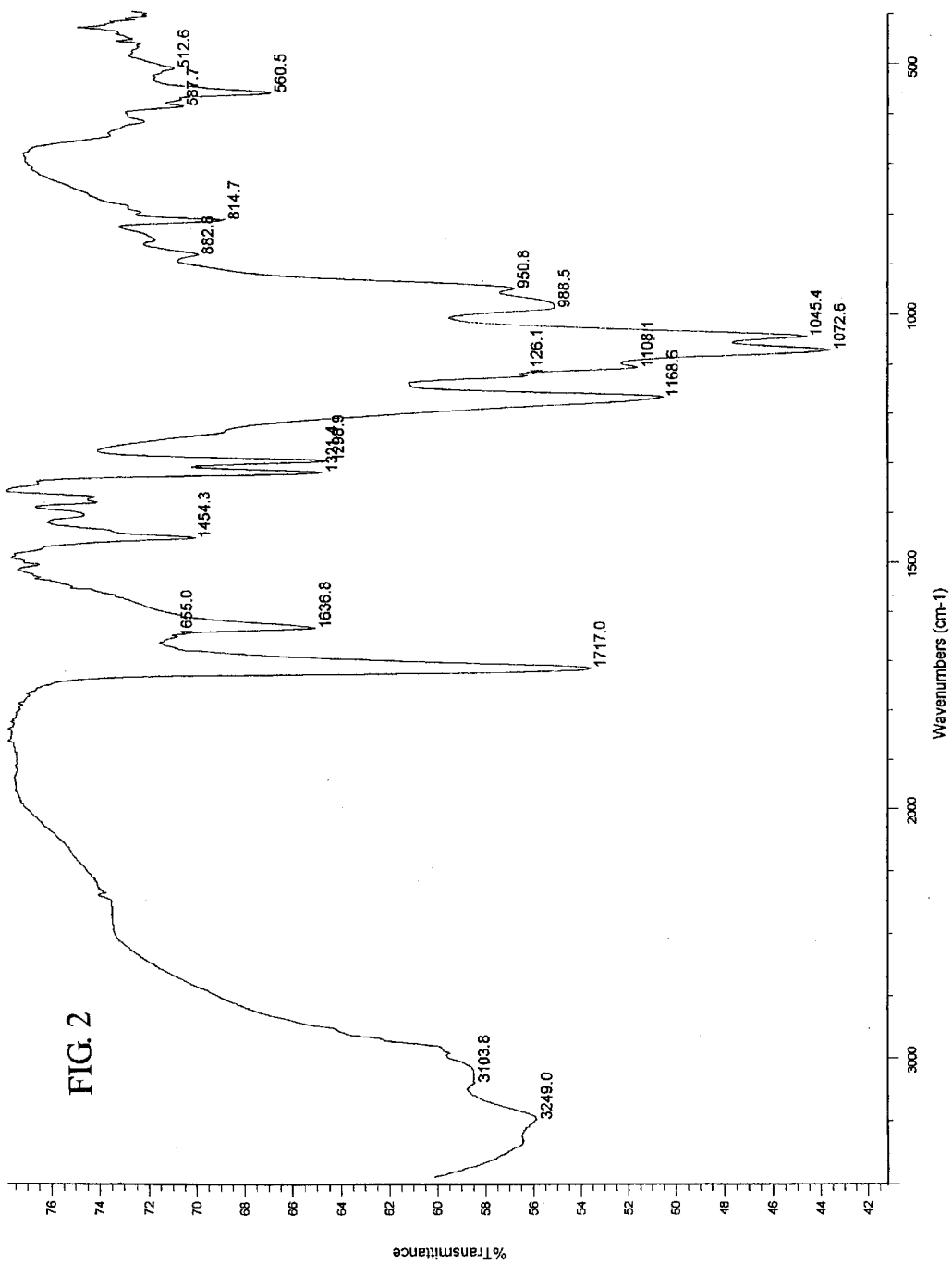
FIG. 2 is an infrared spectrum of a product mixture obtained in Example 1 of the present invention.

To 3 g of water in a 50-ml flask 0.78 g (3.9 mmol) of Cu acetate monohydrate (III) and 1.12 g of a mixture of $H_3PO_4$ mono- and di-ester of 2-hydroxyethyl (meth)acrylate in the form of light yellow oily liquid were added. The mixture of $H_3PO_4$ mono- and di-ester of 2-hydroxyethyl (meth)acrylate contains 1.32 mmol of di-ester (n=1) and 3.31 mmol of mono-ester (n=2), and has an infrared spectrum as shown in FIG. 1. The reaction was carried at room temperature for 4 hours and at 60° C. for one hour, while the reaction mixture was stirring. A blue solid was obtained after the reaction mixture was dried in vacuo, and an infrared spectrum thereof is shown in FIG. 2. The blue solid is believed to contain as a major portion a mixture of complex compounds with n=1 and n=2 in the above formula (I), and unreacted $H_3PO_4$ mono-ester and di-ester (II), because are all non-volatile.

EXAMPLE 2

Figure 3:
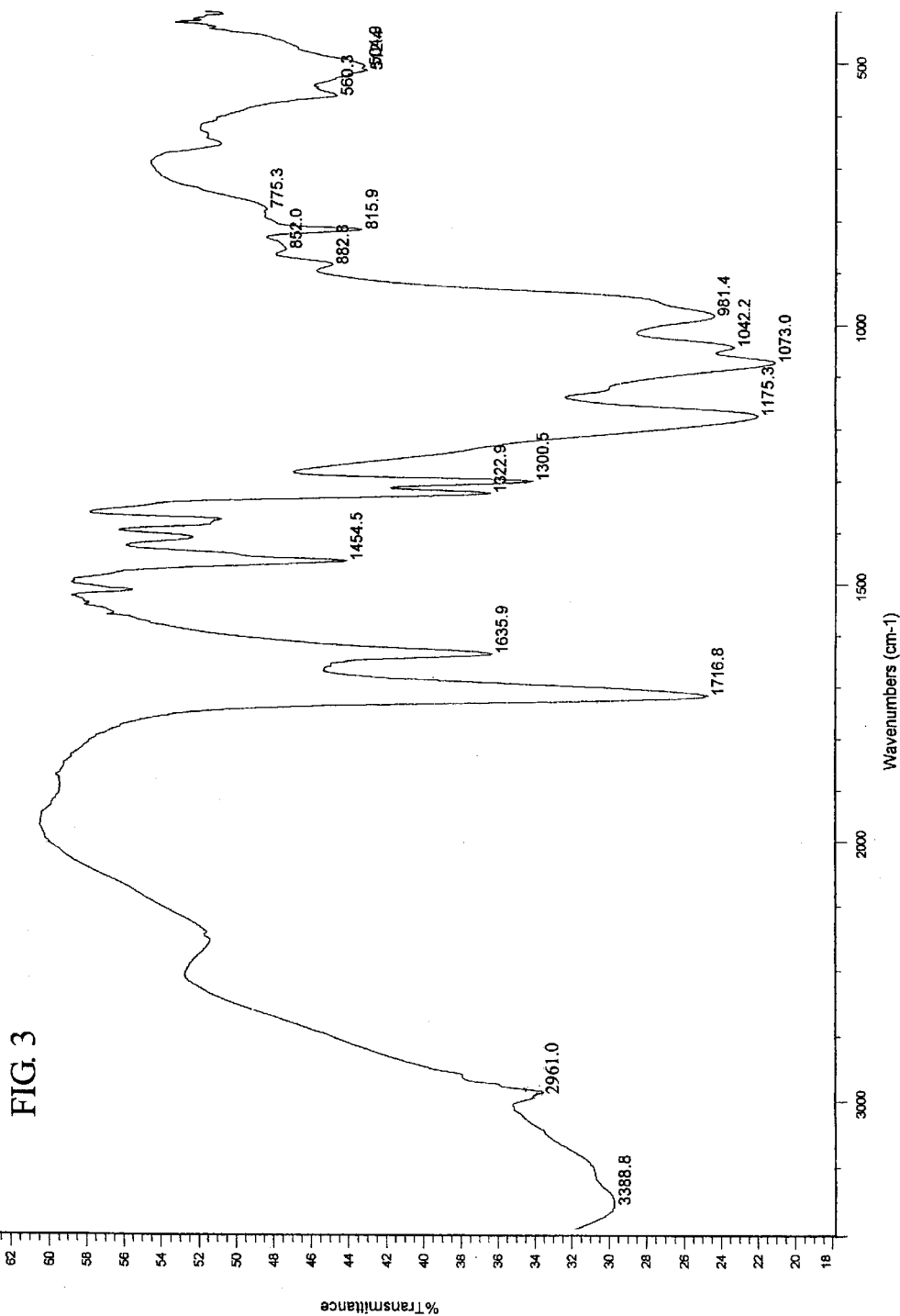
FIG. 3 is an infrared spectrum of a product mixture obtained in Example 2 of the present invention.

To 3 g of water in a 50-ml flask 0.45 g (2.3 mmol) of Cu acetate monohydrate (III) and 1.12 g of a mixture of $H_3PO_4$ mono- and di-ester of 2-hydroxyethyl (meth)acrylate in the form of light yellow oily liquid were added. The mixture of $H_3PO_4$ mono- and di-ester of 2-hydroxyethyl (meth)acrylate contains 1.32 mmol of di-ester (n=1) and 3.31 mmol of mono-ester (n=2). The reaction was carried at room temperature for 4 hours, while the reaction mixture was stirring. A blue paste was obtained after the reaction mixture was dried in vacuo, and an infrared spectrum thereof is shown in FIG. 3. Since less amount of the Cu acetate monohydrate (III) was used in this example in comparison with Example 1, more amount of the oily $H_3PO_4$ mono-ester and di-ester (II) unreacted in the reaction mixture, causing the final product mixture being in the form of a paste.

CONTROL EXAMPLE 1

Figure 4:
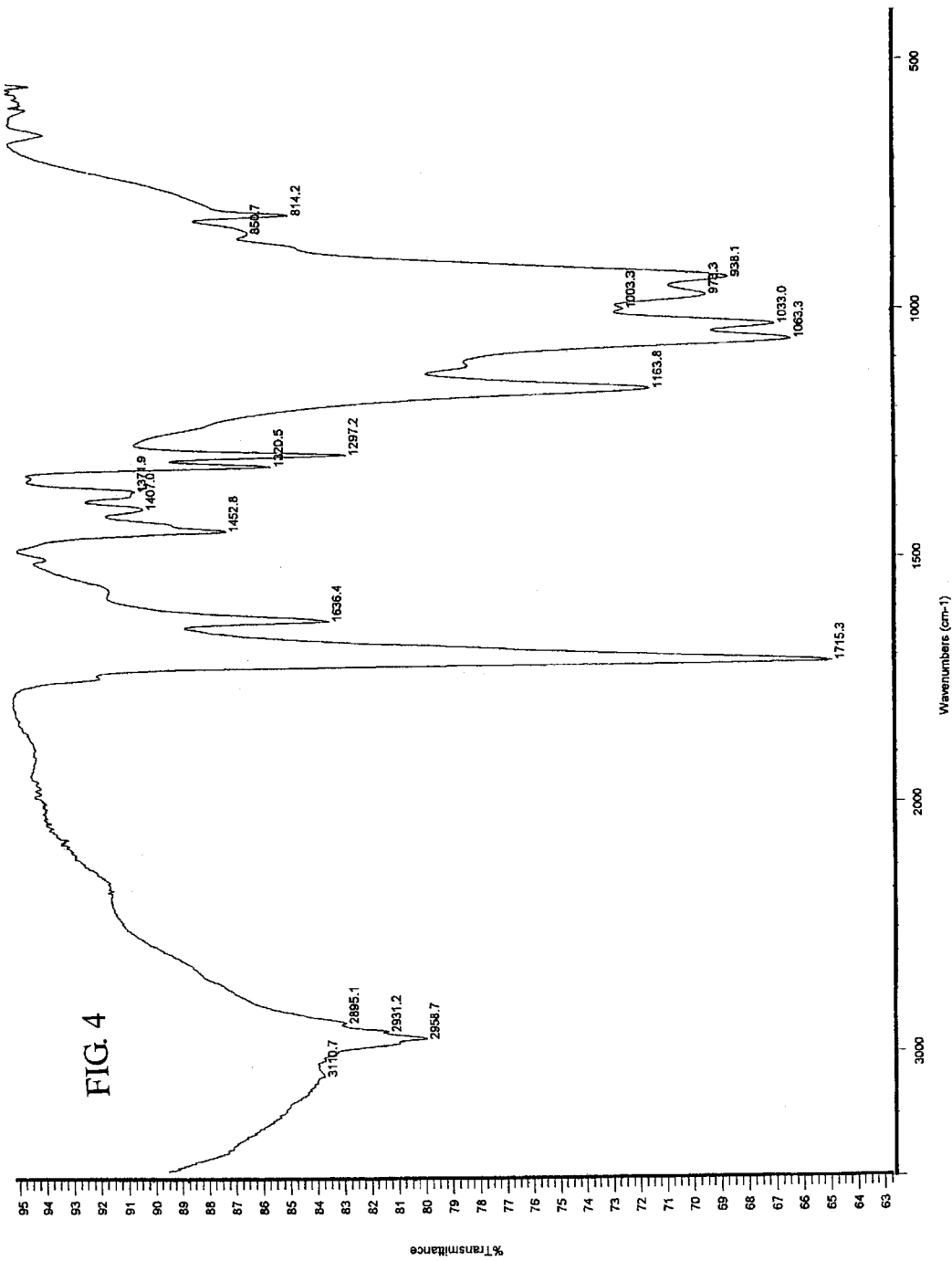
FIG. 4 is an infrared spectrum of a product mixture obtained in control Example 1.

To 20 ml of methyl ethyl ketone in a 50-ml flask 0.16 g (0.8 mmol) of Cu acetate monohydrate (III) and 0.23 g of a mixture of $H_3PO_4$ mono- and di-ester of 2-hydroxyethyl (meth)acrylate in the form of light yellow oily liquid were added. The mixture of $H_3PO_4$ mono- and di-ester of 2-hydroxyethyl (meth)acrylate contains 0.27 mmol of di-ester (n=1) and 0.68 mmol of mono-ester (n=2). The reaction was carried at 50° C. for one hour, while the reaction mixture was stirring. A blue solid was obtained after the reaction mixture was dried in vacuo, and an infrared spectrum thereof is shown in FIG. 4.

It can be readily understood from examples 1–2 and control example 1 that the method of the present invention uses a less amount of water in place of an organic solvent for the same reaction, and successfully synthesizes the same target products.

What is claimed is:

1. A method for preparing a complex having the following formula (I) comprising reacting a $H_3PO_4$ ester of 2-hydroxyethyl (meth)acrylate having the following formula (II) with Cu acetate monohydrate having the following formula (III) in water:

$$R_{3-n}PO(O^-)_nCu(II) \quad (I)$$

wherein R is $CH_2=C(CH_3)COOCH_2CH_2O$, and n is 1 or 2;

$$R_{3-n}PO(OH)_n \quad (II)$$

wherein R and n are defined as above;

$$Cu(CH_3COO)_2 \cdot H_2O \quad (III).$$

2. The method according to claim 1, wherein a mixture of $H_3PO_4$ mono- and di-ester of 2-hydroxyethyl (meth)acrylate with n=1 and n=2 in the formula (II) is reacted with the Cu acetate monohydrate (III) to form a mixture of complex compounds with n=1 and n=2 in the formula (I).

3. The method according to claim 2, wherein said mixture of $H_3PO_4$ mono- and di-ester of 2-hydroxyethyl (meth) acrylate having a molar ratio of the $H_3PO_4$ di-ester of 2-hydroxyethyl (meth)acrylate, n=1, to the $H_3PO_4$ mono-ester of 2-hydroxyethyl (meth)acrylate, n=2, is about 0.4.

4. The method according to claim 1, wherein an amount of the Cu acetate monohydrate (III) used in said reaction is 1%–1000%, based on mole of the $H_3PO_4$ ester (II).

5. The method according to claim 4, wherein the amount of the Cu acetate monohydrate (III) used in said reaction is 40–90%, based on mole of the $H_3PO_4$ ester (II).

6. The method according to claim 1, wherein an amount of water used in said reaction is 0.5–100 times of weight of said $H_3PO_4$ ester (II).

7. The method according to claim 6, wherein said amount of water used in said reaction is 3–4 times of weight of said $H_3PO_4$ ester (II).

8. The method according to claim 1, wherein said reaction is carried out at a temperature between 0 to 100° C.

9. The method according to claim 8, wherein said reaction is carried out at a temperature between 25 to 60° C.

* * * * *